United States Patent [19]

Ropers

[11] Patent Number: 4,553,937
[45] Date of Patent: Nov. 19, 1985

[54] TOOTH MATRIX BAND

[76] Inventor: Till Ropers, Alter Marktplatz 4, D-2162 Steinkirchen, Fed. Rep. of Germany

[21] Appl. No.: 625,072

[22] Filed: Jun. 27, 1984

[30] Foreign Application Priority Data

Jun. 27, 1983 [DE] Fed. Rep. of Germany ....... 3323085

[51] Int. Cl.⁴ .............................................. A61C 5/04
[52] U.S. Cl. ..................................................... 433/39
[58] Field of Search .......................................... 433/39

[56] References Cited

U.S. PATENT DOCUMENTS

| 278,674 | 5/1883 | Wiesbauer | 433/39 |
| 2,353,747 | 7/1944 | Morrison | 433/39 |
| 3,854,210 | 12/1974 | Franklin et al. | 433/39 |

Primary Examiner—John J. Wilson
Attorney, Agent, or Firm—Karl F. Ross; Herbert Dubno

[57] ABSTRACT

A matrix band for encircling a tooth to define a wall of a cavity to be supplied with a filling has reduced thickness end portions. A toothed tongue of reduced width on one end portion can be fitted into a slot in the tab formed by the other reduced width end portion to enable the band to be drawn tightly around a tooth.

9 Claims, 6 Drawing Figures

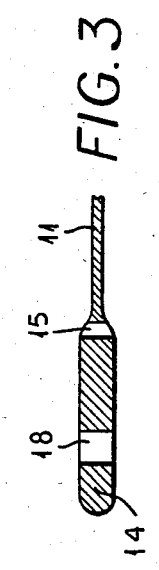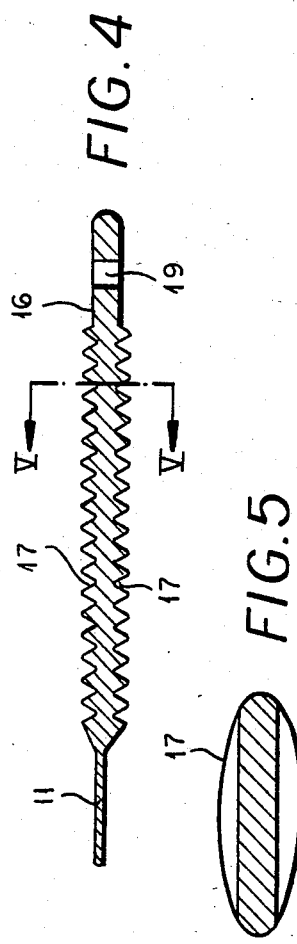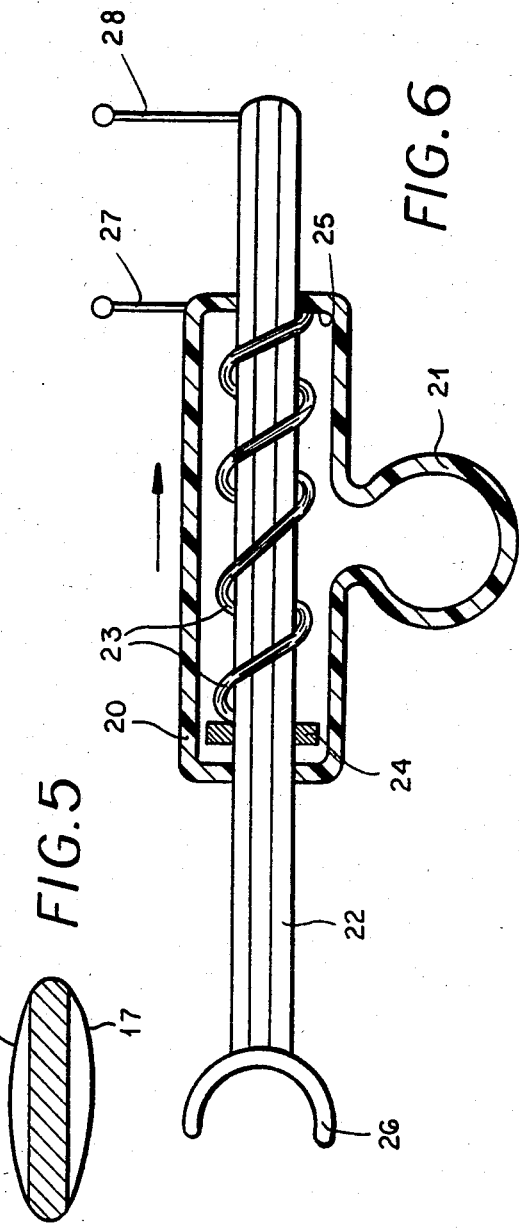

TOOTH MATRIX BAND

FIELD OF THE INVENTION

My present invention relates to a tooth matrix band and, more particularly, to an aid in the filling of teeth to define the periphery of a filled tooth.

BACKGROUND OF THE INVENTION

It is known to provide a band which is adapted to encircle a tooth being filled to support weak walls of the tooth following drilling against the outward forces which are applied during the compression of the filling material into the cavity drilled in a tooth. Such bands are most frequently used to define the outer wall of the cavity when the cavity drilled into the tooth extends to any lateral surface thereof.

Such bands are frequently called matrix bands, are wholly composed of a noncorroding metal such as stainless steel, and have frequently been designed for repeated use.

In the preparation of a tooth which has deteriorated or been the subject of caries, it is a common practice, utilizing dental drills, to remove the deteriorating or deteriorated material to clean enamel and thereby form an undercut cavity of the type described. When the cavity opens solely at the chewing surface of the tooth, the use of a matrix band is not necessary. When, however, the cavity extends to a lateral portion of the tooth, such a matrix band can be applied to define a lateral wall of the cavity into which the filling is forced so that the filling will lie generally flush with the lateral edges of the cavity.

Various matrix bands have been provided heretofore to ensure the correct bite for teeth being repaired, to support the tooth against the mechanical working which ensures the effective strength of amalgam fillings and to separate one filling from another or the filling material of one tooth from an adjacent tooth.

While such matrix bands have been provided in a variety of sizes and shapes, they all are generally associated with a tightening mechanism, generally utilizing screw or wind-up principles, which is normally left in the mouth or may be part of a tool withdrawn from the mouth and which, upon tightening, draws the ends of the band toward one another to tighten the band around the tooth.

OBJECTS OF THE INVENTION

It is the principal object of the present invention to provide an improved matrix band for the purposes described whereby prior art disadvantages may be obviated.

Another object of this invention is to provide a matrix band anchoring assembly which is simple to use and is more versatile than arrangements used heretofore.

Another object of this invention is to provide an improved matrix band which can be put in place by hand and even tightened by hand if desired.

SUMMARY OF THE INVENTION

These objects are attained, in accordance with the present invention, in a matrix band having a relatively wide tooth-encircling central portion, preferably of the configuration of a so-called *Dentatus Nystrom* matrix band which is provided with a pair of end portions of reduced width integral and unitary therewith, one of these end portions being formed with a slot adapted to extend vertically or parallel to a generatrix of the tooth and to receive the reduced-width opposite end portion which can be passed through this slot or slit to enable the tooth-encircling portion to be tightened around the tooth.

According to a feature of the invention, the first or slit-containing end will thus have a greater width or height than the end received in the slit and hereinafter referred to as the tongue. Preferably, moreover, that slit is provided at the junction or transition region between the slit-containing end and the central portion of the band, this end portion of the band being referred to hereinafter also as the tab.

The tongue can be formed with fine-edged steps or teeth to allow indexed anchoring of the tongue within the slit, thereby enabling the band to compensate for teeth of different diameters. Preferably both end portions of the band, which are adapted to take up considerable stress on tightening, can be made thicker than the central portion and preferably about four times as thick.

A tool for use in resistance in tightening the band around the tooth can include a pair of pins which are spread apart and which engage in respective holes in the tab and tongue.

BRIEF DESCRIPTION OF THE DRAWING

The above and other objects, features and advantages of the present invention will become more readily apparent from the following description in which:

FIG. 3 is a cross-sectional view taken along the line III—III of FIG. 1 drawn to a much larger scale and indeed exaggerated in scale;

FIG. 4 is a cross-sectional view along the line IV-IV of FIG. 1, also drawn to an exaggerated scale;

FIG. 5 is a section along the line V-V of FIG. 4; and

FIG. 6 is a partial longitudinal section illustrating a device for tightening the band of the invention.

SPECIFIC DESCRIPTION

Figure 1:
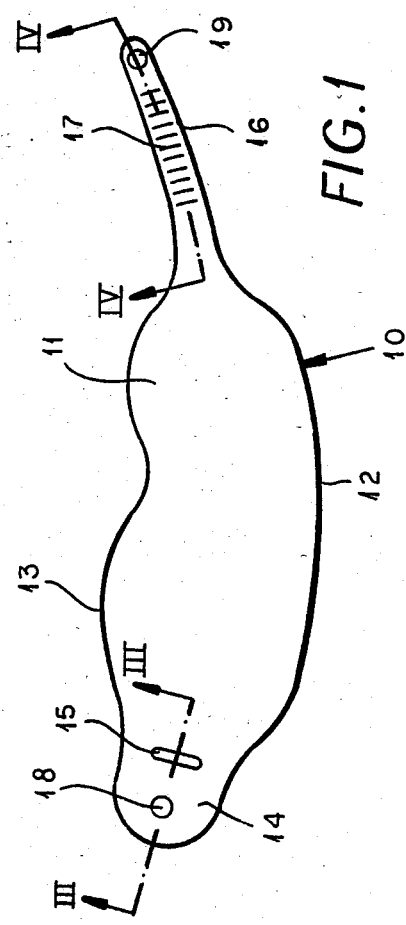
FIG. 1 is an elevational view, fully developed or opened out, of a *Dentatus Nystrom* type matrix band according to the invention.

From FIG. 1 it can be seen that the band 10 generally comprises a central portion 11 of a thickness of about 0.3 mm which is comparatively wide or, as seen in place in the mouth, comparatively high, bounded by a semi-curved arcuate edge 12 and an undulating longitudinal edge 13 in accordance with the principle of the *Dentatus Nystrom* band.

Figure 2:
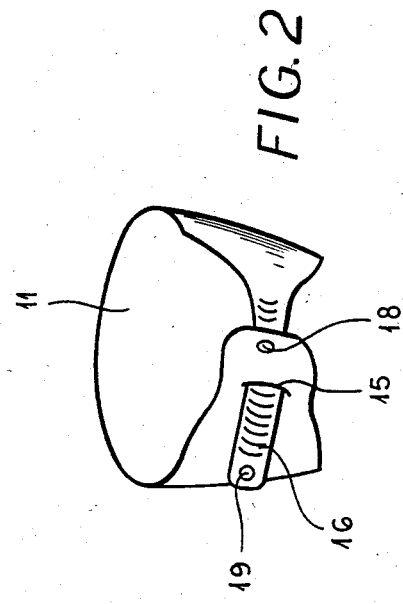
FIG. 2 is a perspective view showing the band in an encircling position to illustrate its use.

Unlike the *Dentatus Nystrom* band, which has identical tongues at each end, at one end of the band 10, I provide an end portion or tab 14 of a width less than the width of the central portion 11 and formed with a slot 15 which, as can be seen from FIG. 2, lies generally vertically along a generatrix of a tooth which may be encircled by this band. The length of this slot 15 corresponds essentially to the width of the tongue 16 formed on the opposite end portion. A row of teeth represented at 17 is formed along the tongue 16 and both end portions are provided with holes 18, 19.

As can be seen from FIG. 2, in operation, the central portion 11 is used to encircle a tooth, a tongue 16 is inserted through the slot 15 and the free end of the tongue 16 emerging from the slot can be drawn to the left manually to tighten the band on the tooth, the teeth serving to retain the band in its encircling tightened positions during filling of the cavity. A forced expansion of the band will enable the tongue 16 to pull out of the slot and allow for disposal of the band which can be composed of stainless steel or any other nontoxic metal or material capable of withstanding the amalgam compaction forces.

As can be seen from FIGS. 3 and 4, the thicknesses of the tab 14 and the tongue 16 are greater than that of the central portion and preferably about four times greater. The slot 15 is seen from FIG. 3 to be located substantially at the partition region between the thicker portion and the thinner portion. The teeth 17, as can be seen from FIG. 5, can be formed as cuts in the upper and lower surface of the generally oval cross section tongue.

The tool which can assist in tightening the encircling band of FIG. 2 has been illustrated diagrammatically in FIG. 6 and comprises a sleeve 20 which can be engaged by a finger entering a finger hole 21. Within this sleeve, a rod 22 is slidable against the force of a spring 23 which is seated against a shoulder 24 of the rod and braced against an end 25 of the sleeve. A thumb pocket 26 can receive the thumb of the dental practitioner. With the band in the position shown in FIG. 2, the radial pins 27 and 28 on the sleeve 20 and upon the rod 22 are inserted into the holes 18 and 19 and the rod 22 is pressed to the right to spread the pins apart and tighten the band around the tooth.

I claim:

1. A matrix band adapted to encircle a tooth comprising a tooth-encircling central portion formed unitarily with a pair of end portions, one of said end portions being of a width less than that of said central portion and constituting a tab provided with a slot adapted to extend substantially vertical upon said band encircling a tooth, the other of said end portions being of a width less than that of said central portion and of said tab, said other of said end portions forming a tongue adapted to pass through and anchor in said slot whereby upon passage of said tongue through said slot said band can be tightened around a tooth by pulling on said tongue relative to said tab, said end portions having greater thicknesses than said central portion.

2. The matrix band defined in claim 1 wherein said slot is provided substantially in the region of a junction between said tab and said central portion.

3. The matrix band defined in claim 2 wherein said tongue is provided with an array of fine-edged steps forming teeth restricting withdrawal of said tongue from said slot.

4. The matrix band defined in claim 1 wherein said tongue is provided with an array of fine-edged steps forming teeth restricting withdrawal of said tongue from said slot.

5. The matrix band defined in claim 1 wherein each of said end portions has a thickness substantially four times greater than that of said central portion.

6. A matrix band assembly comprising a matrix band adapted to encircle a tooth comprising a tooth-encircling central portion formed unitarily with a pair of end portions, one of said end portions being of a width less than that of said central portion and constituting a tab provided with a slot adapted to extend substantially vertical upon said band encircling a tooth, the other of said end portions forming a tongue adapted to pass through and anchor in said slot whereby upon passage of said tongue through said slot said band can be tightened around a tooth by pulling on said tongue relative to said tab, said tongue being of a width less than that of said central portion and said tab and a tool engageable with said tab and said tongue for tightening said band by drawing said tab through said slot, said end portions having greater thicknesses than said central portion.

7. The assembly defined in claim 6 wherein said tab and said tongue have respective holes, said tool comprising a pair of pins which are spreadable apart movably engageable in said holes.

8. The assembly defined in claim 7 wherein said tongue is formed with fine-edged teeth spaced along the length thereof.

9. The matrix band assembly defined in claim 6 wherein each of said end portions has a thickness substantially four times greater than that of said central portion.

* * * * *